US012755822B2

(12) United States Patent
Zhao et al.

(10) Patent No.: US 12,755,822 B2
(45) Date of Patent: Oct. 6, 2026

(54) DEEP LEARNING BASED PCCT IMAGE VIEWER

(71) Applicant: Siemens Healthineers AG, Forchheim (DE)

(72) Inventors: Gengyan Zhao, Plainsboro, NJ (US); Andreea Elena Sandu, Brasov (RO); Eli Gibson, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 253 days.

(21) Appl. No.: 18/581,427

(22) Filed: Feb. 20, 2024

(65) Prior Publication Data

US 2025/0266139 A1 Aug. 21, 2025

(51) Int. Cl.

*G16H 15/00* (2018.01)
*G06T 7/00* (2017.01)
*G16H 10/60* (2018.01)
*G16H 30/40* (2018.01)
*G16H 50/20* (2018.01)

(52) U.S. Cl.

CPC ........... *G16H 15/00* (2018.01); *G06T 7/0012* (2013.01); *G16H 10/60* (2018.01); *G16H 30/40* (2018.01); *G16H 50/20* (2018.01)

(58) Field of Classification Search

CPC ........ G16H 15/00; G16H 10/60; G16H 50/20; G16H 30/40; G06T 7/0012
See application file for complete search history.

(56) References Cited

U.S. PATENT DOCUMENTS

2020/0074712 A1* 3/2020 Wu ........................... G06T 3/60
2024/0212812 A1* 6/2024 Vidyashankar Keresanthe ........... G16H 30/40
2025/0029707 A1* 1/2025 Park ....................... G16H 30/40
2025/0102788 A1* 3/2025 Amthor .................. G06N 3/045
2025/0232872 A1* 7/2025 Natarajan ............. G16H 20/00

FOREIGN PATENT DOCUMENTS

CN 117558416 A 2/2024

OTHER PUBLICATIONS

Flohr et al., "Photon-counting CT review", Physica Medica, 2020, pp. 26-136.

(Continued)

*Primary Examiner* — David F Dunphy

(57) ABSTRACT

Systems and methods for generating a guided review of the one or more input medical images are provided. One or more input medical images of a patient and text-based patient data of the patient are received. One or more clinical tasks are identified based on the text-based patient data using a language model. One or more machine learning based models are selected based on the one or more identified clinical tasks. One or more medical imaging analysis tasks are performed based on the one or more input medical images using the one or more selected machine learning based models. A guided review of the one or more input medical images is generated based on results of the one or more medical imaging analysis tasks. The guided review of the one or more input medical images is output.

16 Claims, 6 Drawing Sheets

(56) References Cited

OTHER PUBLICATIONS

Leng et al., "Photon-counting Detector CT: System Design and Clinical Applications of an Emerging Technology". RadioGraphics, 2019, pp. 729-743.
Willemink et al., "Photon-counting CT: Technical Principles and Clinical Prospects", Radiology, 2018, pp. 1-20.
Chappard et al., "Virtual monoenergetic images from photon-counting spectral computed tomography to assess knee osteoarthritis", European Radiology Experimental, 2022, pp. 1-10.
Extended European Search Report mailed Jul. 9, 2025 in counterpart European Patent Application No. 25158229.2.
Pellegrini Chantal et al: "RaDialog: A Large Vision-Language Model for Radiology Report Generation and Conversational Assistance", arXiv.org, Nov. 1, 2023.
Tian Dianzhe et al: "The role of large language models in medical image processing: a narrative review", Quantitative Imaging in Medicine and Surgery, vol. 14, No. 1, Nov. 23, 2023 (Nov. 23, 2023), pp. 1108-1121, Retrieved from the Internet: URL:https://pmc.ncbi.nlm.nih.gov/articles/PMC10784029/pdf/ qims-14-01-1108.pdf.
Huemann Zachary et al: "ConTEXTual Net: A Multimodal Vision-Language Model for Segmentation of Pneumothorax", Journal of Imaging Informatics in Medicine, vol. 37, No. 4, Sep. 15, 2023 (Sep. 15, 2023), pp. 1652-1663.

* cited by examiner

DEEP LEARNING BASED PCCT IMAGE VIEWER

TECHNICAL FIELD

The present invention relates generally to an AI/ML (artificial intelligence/machine learning) based medical image viewer, and in particular to a DL (deep learning) based PCCT (photon-counting computed tomography) image viewer.

BACKGROUND

PCCT is an imaging technique that uses x-ray detectors to count the number of incoming photons and measure their energy. Compared with standard CT (computed tomography), PCCT provides high-resolution images with improved image quality, greater signal-to-noise ratio, and reduced radiation dose. However, in the current clinical workflow, such high-resolution PCCT images generated by PCCT is typically viewed using conventional image viewers. Such conventional image viewers are unable to utilize the advantages offered by high-resolution PCCT images.

BRIEF SUMMARY OF THE INVENTION

In accordance with one or more embodiments, systems and methods for generating a guided review of the one or more input medical images are provided. One or more input medical images of a patient and text-based patient data of the patient are received. One or more clinical tasks are identified based on the text-based patient data using a language model. One or more machine learning based models are selected based on the one or more identified clinical tasks. One or more medical imaging analysis tasks are performed based on the one or more input medical images using the one or more selected machine learning based models. A guided review of the one or more input medical images is generated based on results of the one or more medical imaging analysis tasks. The guided review of the one or more input medical images is output.

In one embodiment, the guided review comprising a whole-image review of the one or more input medical images, a compartmental review depicting one or more anatomically cropped regions of the one or more input medical images, and a findings review depicting one or more pathologically cropped regions of the one or more input medical images is generated.

In one embodiment, the guided review of the one or more input medical images is presented to a user via a display device. A cropped region depicting a first finding is presented, user input from the user confirming a decision on the first finding is received, and in response to receiving the user input, a cropped region depicting a second finding is automatically depicted. The guided review of the one or more input medical images may be presented according to parameters determined based on the one or more identified clinical tasks and outputs of the one or more selected machine learning based models.

In one embodiment, the language model receives as input the text-based data and generates as output one or more vectors corresponding to the one or more or more clinical tasks. The language model may be an LLM (large language model).

In one embodiment, the one or more machine learning based models are selected from a database of pre-trained machine learning based models. The pre-trained machine learning based models comprise machine learning based models for performing different medical imaging analysis tasks and machine learning based models with different sensitivity.

In one embodiment, the one or more input medical images comprise one or more PCCT (photon-counting computed tomography) images.

These and other advantages of the invention will be apparent to those of ordinary skill in the art by reference to the following detailed description and the accompanying drawings.

DETAILED DESCRIPTION

The present invention generally relates to methods and systems for a deep learning based PCCT image viewer. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for a deep learning based PCCT image viewer. The PCCT image viewer provides an automated or semi-automated guided review of a PCCT image to a radiologist (or any other user) through different anatomical objects and pathological findings. At each step of the guided review, the PCCT image viewer shows an appropriate image of, or derived from, the PCCT image with proper configurations to assist the radiologist in making diagnoses and decisions. Advantageously, the PCCT image viewer accelerates and automates the clinical workflow for PCCT image reading and interpretation by taking advantage of the features offered by PCCT.

Figure 1:
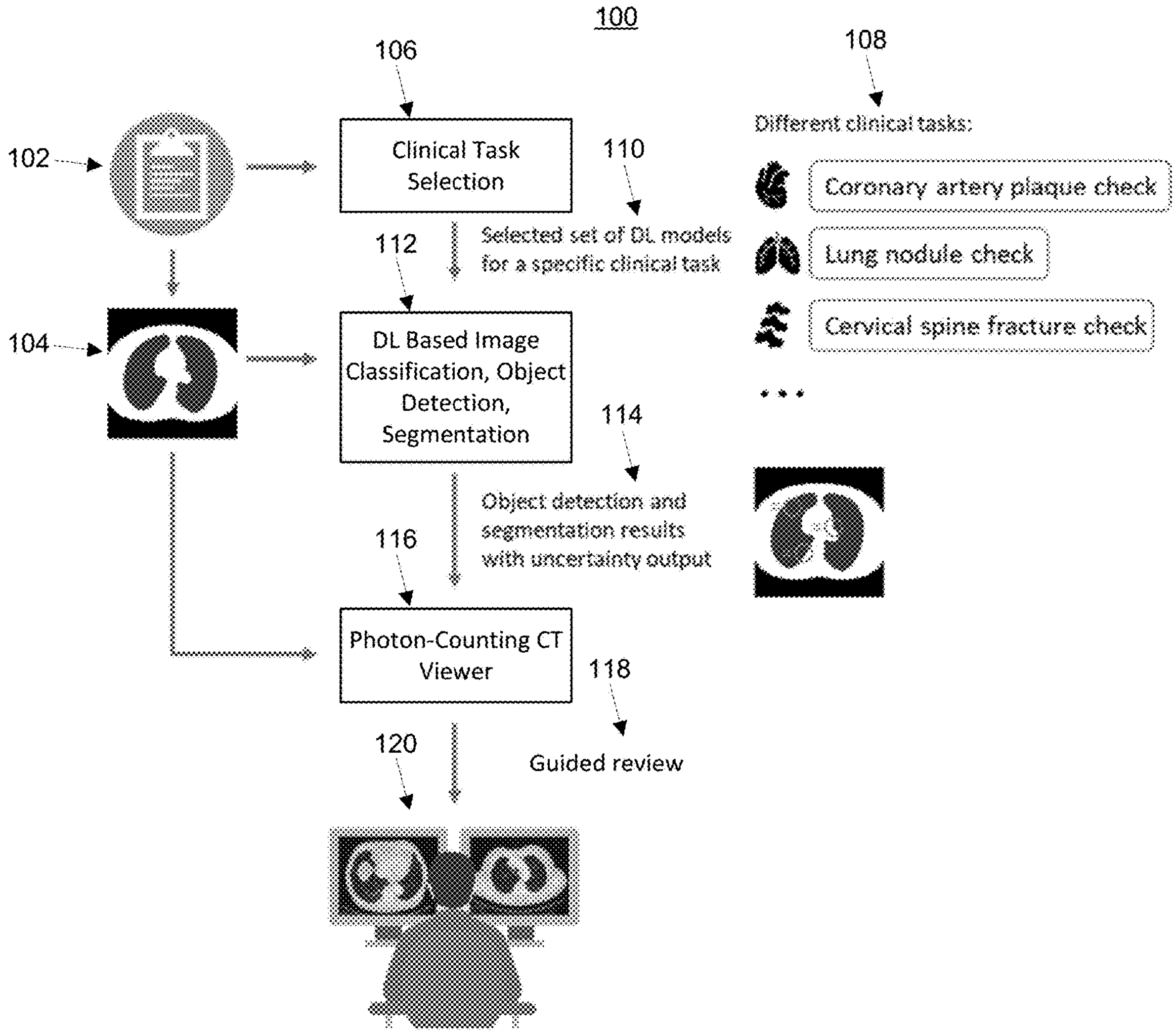
FIG. 1 shows a workflow for generating a guided review of one or more PCCT images, in accordance with one or more embodiments.
Figure 2:
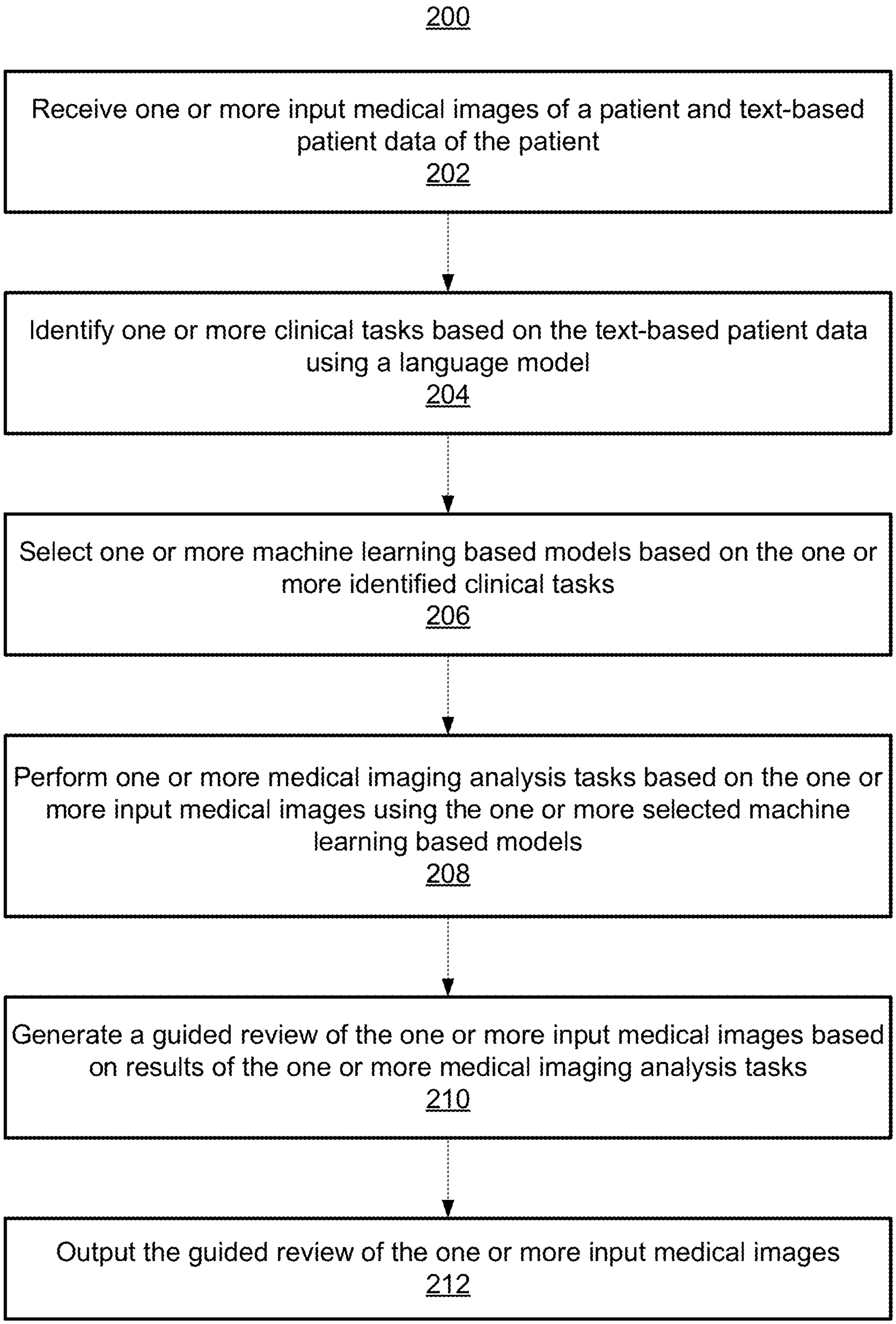
FIG. 2 shows a method for generating a guided review of one or more input medical images, in accordance with one or more embodiments.

FIG. 1 shows a workflow 100 for generating a guided review of one or more PCCT images, in accordance with one or more embodiments. FIG. 2 shows a method 200 for generating a guided review of one or more input medical images, in accordance with one or more embodiments. The steps and sub-steps of method 200 of FIG. 2 may be performed using one or more suitable computing devices, such as, e.g., computer 602 of FIG. 6. FIGS. 1 and 2 will be described together.

At step 202 of FIG. 2, one or more input medical images of a patient and text-based patient data of the patient are received. In one example, as shown in workflow 100 of FIG. 1, the one or more input medical images is PCCT image 104 and the text-based patient data is text-based patient data 102.

The one or more input medical images may depict one or more anatomical objects, such as, e.g., organs, bones, vessels, tumors or other abnormalities, or any other anatomical objects of interest of the patient. In one embodiment, the one or more input medical images comprise PCCT images of the patient. However, the one or more input medical images may be of any other suitable modality, such as, e.g., CT (computed tomography), MRI (magnetic resonance imaging), US (ultrasound), x-ray, or any other medical imaging modality or combinations of medical imaging modalities. The one or more input medical images may comprise 2D (two dimensional) images and/or 3D (three dimensional) volumes.

The text-based patient data may comprise any suitable text-based data of the patient. In one embodiment, the text-based patient data may comprise text-based clinical or radiology reports of the patient, current symptoms experienced by the patient, and current prescription medication the patient is taking. However, the text-based patient data may comprise any other suitable text-based data of the patient, such as, e.g., demographic information, vital signs, medical history, family history, laboratory results, measurements and information extracted from medical images, etc. of the patient.

Figure 6:
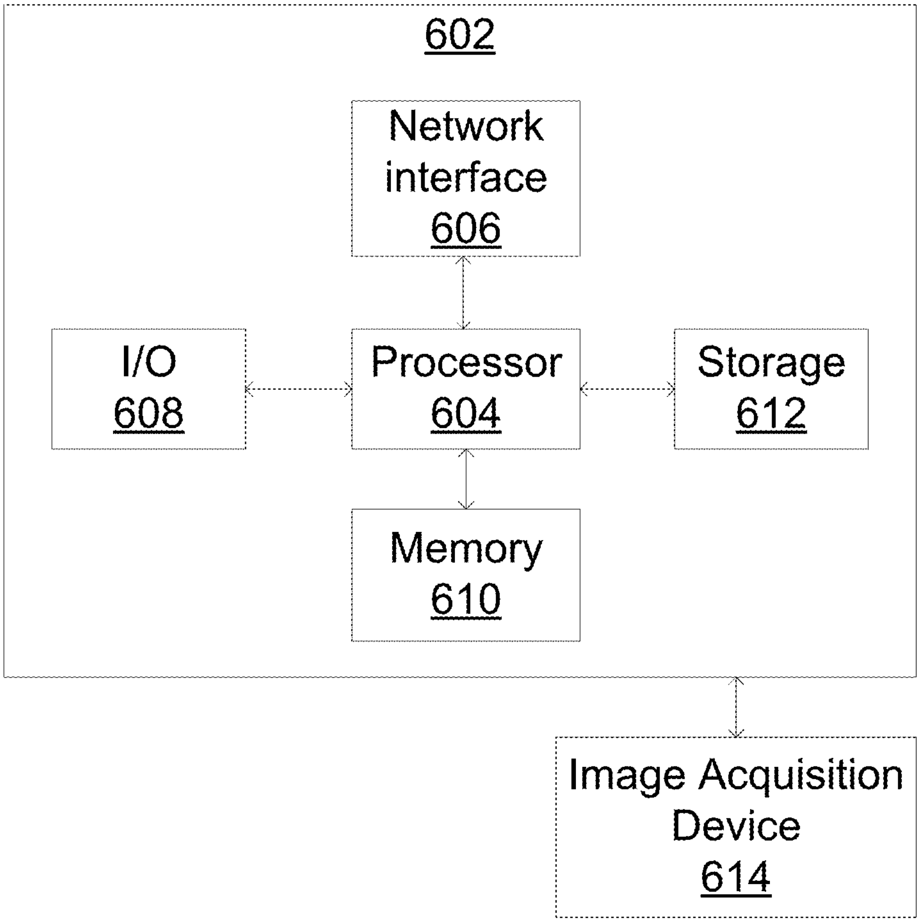
FIG. 6 shows a high-level block diagram of a computer that may be used to implement one or more embodiments.

The one or more input medical images and the text-based patient data may be received, for example, by directly receiving the one or more input medical images from an image acquisition device (e.g., image acquisition device 614 of FIG. 6) as the images are acquired, by loading the one or more input medical images and/or the text-based patient data from a storage or memory of a computer system (e.g., memory 610 or storage 612 of computer 602 of FIG. 6), or by receiving the one or more input medical images and/or the text-based patient data from a remote computer system (e.g., computer 602 of FIG. 6). Such a computer system or remote computer system may comprise one or more patient databases, such as, e.g., an EHR (electronic health record), EMR (electronic medical record), PHR (personal health record), HIS (health information system), RIS (radiology information system), PACS (picture archiving and communication system), LIMS (laboratory information management system), or any other suitable database or system.

At step 204 of FIG. 2, one or more clinical tasks are identified based on the text-based patient data using a language model. In one example, as shown in workflow 100 of FIG. 1, clinical task selection 106 is performed based on text-based patient data 102 to identify clinical tasks 108. As illustratively shown in FIG. 1, clinical tasks 108 comprise coronary artery plaque check, lung nodule check, and cervical spine fracture check.

The language model is an AI/ML based model trained for predicting sequences in the language domain. In one embodiment, the language model is an LLM (large language model). However, the language model may be any other suitable language model. For example, the language model may be a small language model, which uses a relatively smaller neural network, has fewer parameters, and is trained on less training data as compared with an LLM.

The LLM may be any suitable pre-trained deep learning based LLM. For example, the LLM may be based on the transformer architecture, which uses a attention mechanism to capture long-range dependencies in text. One example of a transformer-based architecture is GPT (generative pre-training transformer), which has a multilayer transformer decoder architecture that may be pretrained to optimize the next token prediction task and then fine-tuned with labelled data for various downstream tasks. GPT-based LLMs may be trained and/or fine-tuned using reinforcement learning with human feedback for performing various natural language processing tasks. Other exemplary transformer-based architectures include BLOOM (BigScience Large Open-science Open-access Multilingual Language Model) and BERT (Bidirectional Encoder Representations from Transformers). The LLM is fine-tuned for the medical imaging domain. In some embodiments, the LLM may be a multi-modal LLM to receive, e.g., imaging data (e.g., the one or more input medical images) in addition to the text-based report and the plurality of predefined templates. The pre-training and fine-tuning are performed during a prior offline or training stage or stages. Once trained, the LLM is applied during an online or inference stage, e.g., to perform step 204 of FIG. 2.

The language model receives as input one or more prompts comprising the text-based patient data and generates as output the one or more identified clinical tasks. A prompt refers to input to a language model for generating a response. The prompt may be received, for example, from a computer system via one or more APIs (application programming interfaces) or from a user interacting with a computer system. The one or more identified clinical tasks may be output as one or more numerical vectors. The numerical vectors have a predefined meaning as being associated with the one or more identified clinical tasks learned during the pre-training and/or fine-tuning. However, the one or more clinical tasks may be output in any other suitable format, such as, e.g., a natural language output.

The one or more clinical tasks may be any suitable clinical task for the patient. In one example, for a patient having a severe headache, having had a stroke before, and being prescribed for a head PCCT scan, the one or more clinical tasks may be a brain acute finding task. In another example, for a patient having shortness of breath and chest pain and having had a head attack before, the one or more clinical tasks may be a coronary artery plaque check task.

In one embodiment, a plurality of candidate clinical tasks may be identified using the language model and presented to a user (e.g., a clinician) via a display device. The user may select one or more of the plurality of candidate clinical tasks as the one or more clinical tasks.

At step 206 of FIG. 2, one or more machine learning based models are selected based on the one or more identified clinical tasks. In one example, as shown in workflow 100 of FIG. 1, the one or more selected machine learning based models are selected set of DL models 110 selected for specific clinical tasks 108. For example, for the task of neurotriage in the emergency room, the DL model to detect acute findings (hemorrhage, infarct, mass effect etc.) in the brain is launched.

The one or more machine learning based models are selected from a database of pre-trained machine learning based models. The one or more machine learning based models are for performing any suitable medical imaging analysis task or tasks. In one example, the one or more machine learning based models comprise classification, detection, segmentation, quantification, etc. for specific pathologies or for any other anatomical object of interest. In another example, the one or more machine learning based models comprise high-sensitivity models to exclude the presence of any finding in specific image subregions. In one embodiment, the one or more machine learning based models may also output uncertainty information associated with the model output.

In one example, where the one or more clinical tasks comprise a brain acute finding task, a machine learning based image classification model may be selected for classifying acute hemorrhage, infarct, and mass effect. If any of the acute hemorrhage, infarct, or mass effect is classified as being positive, a machine learning based segmentation model may be selected to segment the positive finding. The machine learning based models respectively generate as output classification results and segmentation maps, as well as the corresponding uncertainty. A high-sensitivity machine learning based extracranial finding model may be selected for, e.g., excluding the presence of findings inferior to the foramen magnum.

In another example, where the one or more clinical tasks comprise a coronary artery plaque check task, a machine learning based coronary artery plaque detection model may be selected for detecting coronary artery plaques in a PCCT image. The machine learning based coronary artery plaque detection model generates as output bounding boxes around the detected coronary artery plaques, as well as the corresponding uncertainty.

The one or more machine learning based models are pre-trained during a prior offline or training stage. Once trained, the one or more machine learning based models are stored in a database (e.g., storage 610 or 612 of computer 602 of FIG. 6) of machine learning based models and applied during an online or inference stage, e.g., to perform step 208 of FIG. 2 (described in further detail below).

At step 208 of FIG. 2, one or more medical imaging analysis tasks are performed based on the one or more input medical images using the one or more selected machine learning based models. The one or more medical imaging analysis task may comprise any suitable medical imaging analysis task, such as, e.g., detection, classification, segmentation, quantification, etc. of an anatomical object (e.g., a pathology). In one example, as shown in workflow 100 of FIG. 1, the one or more medical imaging analysis tasks comprise DL based image classification, object detection, and segmentation tasks 112 performed based on PCCT image 104 to generate object detection and segmentation results with uncertainty output 114. The one or more selected machine learning based models receive as input the one or more input medical images and generate as output results of a medical imaging analysis task. The results of the medical imaging analysis tasks may comprise, or be used to generate, anatomical findings and pathological findings of the one or more input medical images.

At step 210 of FIG. 2, a guided review of the one or more input medical images is generated based on results of the one or more medical imaging analysis tasks. In one example, as shown in workflow 100 of FIG. 1, a guided review 118 of PCCT image 104 is generated by photo-counting CT viewer 116 based on object detection and segmentation results with uncertainty output 114.

The guided review comprises steps in a preferred order with automatic rendering. In one embodiment, stages of the guided review comprise a whole-image review of each of the one or more input medical images, a compartmental review depicting an anatomically cropped region(s) of anatomical findings of the one or more input medical images, and a findings reviews depicting pathologically cropped region(s) of pathological findings the one or more input medical images. The anatomically cropped region(s) and the pathologically cropped regions are cropped based on results of the one or more medical imaging analysis tasks. For example, the cropped region(s) may be regions of a predefined size cropped around segmentation results, detection results, a bounding box, etc.

In one example, the guided review may begin with a whole image review of the one or more input medical images at a standard resolution, then the one or more input medical images will be zoomed in to a cropped region depicting a first finding. After receiving user input from a user confirming that a decision or diagnosis on the first finding is received, the one or more input medical images will be zoomed out and then zoomed in to cropped region depicting a second finding. After receiving user input from the user confirming that a decision or diagnosis of the second finding is received, the one or more input medical images will be zoomed out and then zoomed in to a cropped region depicting a third finding. The guided review will continue accordingly to the remaining findings. At each stage, viewer parameters (e.g., reconstruction resolution, zoom level, window/level, overlay selection) of the image viewer for presenting the guided review will be determined by the clinical task and by the model outputs (e.g., finding scale and uncertainty). The high-resolution image information from the PCCT images may be used as appropriate to balance the clinical benefit of additional information with the time cost of reviewing the additional information. The proper image from PCCT is shown during this procedure according to the diagnosis task, e.g., the original PCCT image is shown or the material decomposition image is shown for an iodine contrast enhanced imaging task.

For the findings review, if the uncertainty of a finding from the machine learning based model is high or if the finding itself is of a small size (e.g., as compared to a threshold), the finding in an ultra-high-resolution PCCT image may be zoomed in at a high level to show the details of the finding. If the uncertainty of the finding from the machine learning based model is low or if the finding itself is of a large size (e.g., as compared to a threshold), the finding in the PCCT image may be zoomed in at a standard level to show the whole picture of the finding and accelerate diagnosis. For example, for a small lung nodule with high detection uncertainty, the finding on the PCCT image will be zoomed in at a high level to show the details. In this way, the ultra-high resolution of the PCCT image is taken advantage of to optimize the workflow of the radiologist.

In addition to the usage of the ultra-high resolution of the PCCT image, the corresponding type of image derived from the PCCT image may be loaded and shown automatically for different types of compartments or findings predicted by the machine learning based models. For example, where the finding is calcified coronary artery plaque, the calcium map derived from the PCCT image acquisition will be used. Where the finding is a coronary stent in a CT angiography, the iodine map will be shown. Where the finding is knee osteoarthritis, the virtual monoenergetic images at 60 keV (kilo-electronvolt) is calculated and shown, since it provides sufficient soft-tissue contrast to characterize surfaces, disruption, calcification of cartilage, bone osteophytes, and bone cysts and the volume and density of bone cysts can be quantified.

At step 212 of FIG. 2, the guided review of the one or more input medical images is output. In one embodiment, the guided review is output by presenting the guided review to a user on a display device (e.g., I/O 608 of FIG. 6). In one example, as shown in workflow 100 of FIG. 1, guided review 118 of PCCT image 104 is presented 120 to a user. However, the guided review may also be output by, for example, storing the guided review on a memory or storage of a computer system (e.g., memory 610 or storage 612 of computer 602 of FIG. 6), or by transmitting guided review to a remote computer system (e.g., computer 602 of FIG. 6).

Advantageously, the image viewer for generating a guided review of one or more input medical images in accordance with embodiments described herein is oriented for clinical workflows. The image viewer is not merely for viewing medical images, but optimizes and accelerates clinical workflows. Using a language model for clinical task selection and machine learning based models for performing medical imaging analysis tasks, the image viewer generates a guided review of the one or more input medical images to guide a radiologist for identifying where to focus and what to look for while walking the radiologist through each finding to facilitate clinical decisions. Where additional information is not needed, a faster review of less information is enabled. In this way, the clinical workflow for radiology can be optimized and accelerated by the image viewer.

Further, the image viewer in accordance with embodiments described herein is empowered by machine learning based models. Different sets of machine learning based models are used for different clinical tasks. Results of medical imaging analysis tasks output by the machine learning based models, along with corresponding uncertainty information, are used to optimize the clinical workflow and visualization of PCCT image.

In addition, the image view in accordance with embodiments described herein takes advantage of the extra information provided by PCCT images. Using different machine learning based models, different types of images (e.g., ultra-high resolution PCCT images, material decomposed images, and virtual monoenergetic images of a PCCT image) from PCCT is shown in the image viewer with proper configuration (e.g., the zoom level, the material for the material decomposed image, the keV for the virtual monoenergetic image, etc.) to best facilitate and accelerate the diagnosis workflow.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., selected set of DL models 110 of FIG. 1 and the language model utilized at step 204 and the one or more machine learning based models selected and applied at steps 206 and 208 of FIG. 2, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 3:
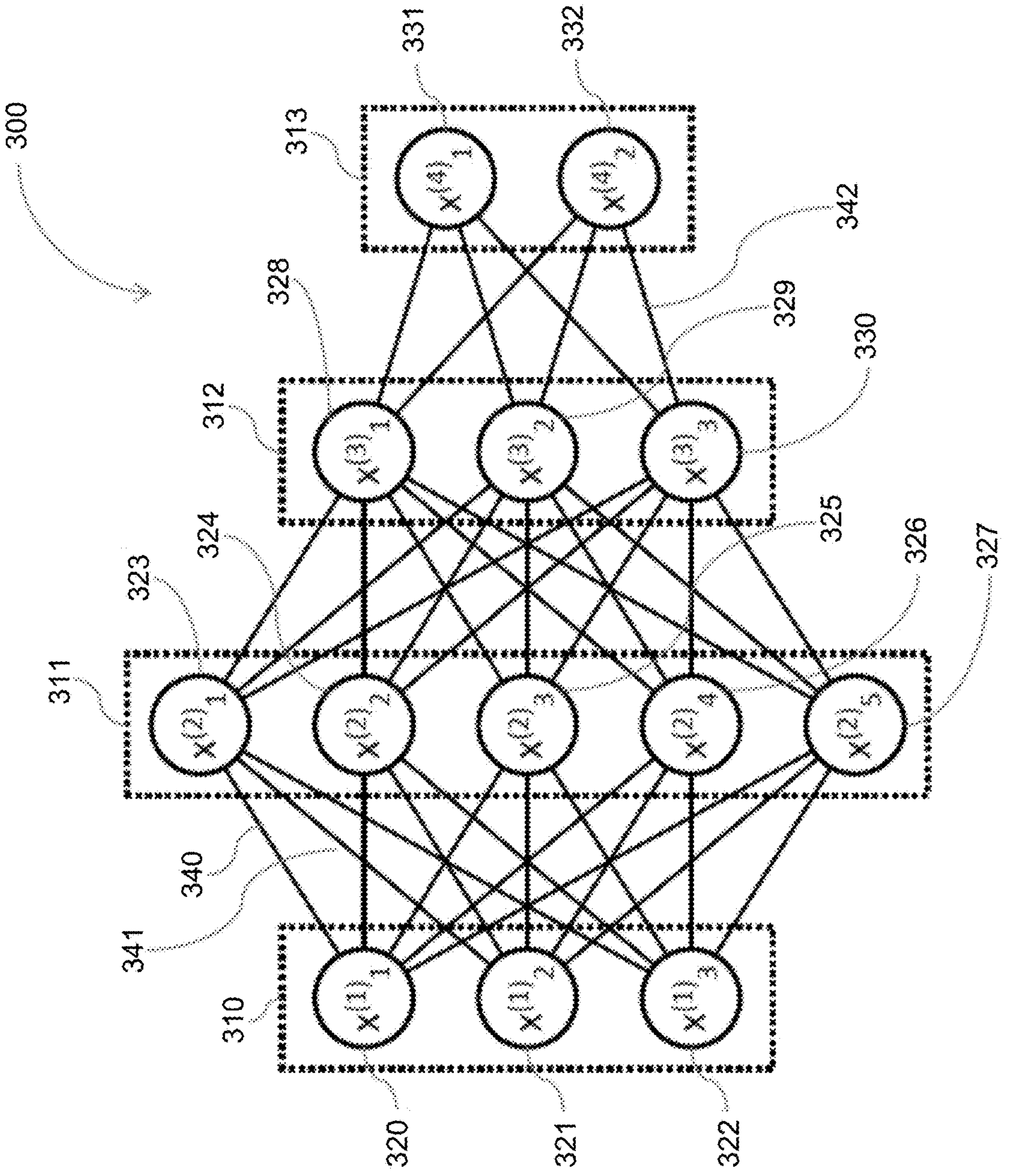
FIG. 3 shows an exemplary artificial neural network that may be used to implement one or more embodiments.

FIG. 3 shows an embodiment of an artificial neural network 300 that may be used to implement one or more machine learning models described herein. Alternative terms for "artificial neural network" are "neural network", "artificial neural net" or "neural net".

The artificial neural network 300 comprises nodes 320, . . . , 332 and edges 340, 342, wherein each edge 340, . . . , 342 is a directed connection from a first node 320, . . . 332 to a second node 320, . . . , 332. In general, the first node 320, . . . , 332 and the second node 320, . . . 332 are different nodes 320, . . . , 332, it is also possible that the first node 320, . . . , 332 and the second node 320, . . . , 332 are identical. For example, in FIG. 3 the edge 340 is a directed connection from the node 320 to the node 323, and the edge 342 is a directed connection from the node 330 to the node 332. An edge 340, . . . , 342 from a first node 320, . . . , 332 to a second node 320, . . . , 332 is also denoted as "ingoing edge" for the second node 320, . . . , 332 and as "outgoing edge" for the first node 320, . . . , 332.

In this embodiment, the nodes 320, . . . , 332 of the artificial neural network 300 can be arranged in layers 310, . . . , 313, wherein the layers can comprise an intrinsic order introduced by the edges 340, . . . , 342 between the nodes 320, . . . , 332. In particular, edges 340, . . . , 342 can exist only between neighboring layers of nodes. In the displayed embodiment, there is an input layer 310 comprising only nodes 320, . . . , 322 without an incoming edge, an output layer 313 comprising only nodes 331, 332 without outgoing edges, and hidden layers 311, 312 in-between the input layer 310 and the output layer 313. In general, the number of hidden layers 311, 312 can be chosen arbitrarily. The number of nodes 320, . . . , 322 within the input layer 310 usually relates to the number of input values of the neural network, and the number of nodes 331, 332 within the output layer 313 usually relates to the number of output values of the neural network.

In particular, a (real) number can be assigned as a value to every node 320, . . . , 332 of the neural network 300. Here, $$x^{(n)}{}_i$$

denotes the value of the i-th node 320, . . . , 332 of the n-th layer 310, . . . , 313. The values of the nodes 320, . . . , 322 of the input layer 310 are equivalent to the input values of the neural network 300, the values of the nodes 331, 332 of the output layer 313 are equivalent to the output value of the neural network 300. Furthermore, each edge 340, . . . , 342 can comprise a weight being a real number, in particular, the weight is a real number within the interval [−1, 1] or within the interval [0, 1]. Here, $$w^{(m,n)}{}_{i,j}$$

denotes the weight of the edge between the i-th node 320, . . . , 332 of the m-th layer 310, . . . , 313 and the j-th node 320, . . . , 332 of the n-th layer 310, . . . , 313. Furthermore, the abbreviation $$w^{(n)}{}_{i,j}$$

is defined for the weight $$w^{(n,n+1)}{}_{i,j}.$$

In particular, to calculate the output values of the neural network 300, the input values are propagated through the neural network. In particular, the values of the nodes 320, . . . , 332 of the (n+1)-th layer 310, . . . , 313 can be calculated based on the values of the nodes 320, . . . , 332 of the n-th layer 310, . . . , 313 by $$x^{(n+1)}{}_j = f\left(\sum_i x^{(n)}{}_i \cdot w^{(n)}{}_{i,j}\right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 310 are given by the input of the neural network 300, wherein values of the first hid-den layer 311 can be calculated based on the values of the input layer 310 of the neural network, wherein values of the second hidden layer 312 can be calculated based in the values of the first hidden layer 311, etc.

In order to set the values $$w^{(m,n)}{}_{i,j}$$

for the edges, the neural network 300 has to be trained using training data. In particular, training data comprises training input data and training output data (denoted as $t_i$). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w'^{(n)}{}_{i,j} = w^{(n)}{}_{i,j} - \gamma \cdot \delta^{(n)}{}_j \cdot x^{(n)}{}_i$$

wherein y is a learning rate, and the numbers $\delta^{(n)}{}_j$ can be recursively calculated as $$\delta^{(n)}{}_j = \left(\sum_k \delta^{(n+1)}{}_k \cdot w^{(n+1)}{}_{j,k}\right) \cdot f'\left(\sum_i x^{(n)}{}_i \cdot w^{(n)}{}_{i,j}\right)$$

based on $\delta^{(n+1)}{}_j$, if the (n+1)-th layer is not the output layer, and $$\delta^{(n)}{}_j = \left(x^{(n+1)}{}_j - t^{(n+1)}{}_j\right) \cdot f'\left(x^{(n)}{}_i \cdot w^{(n)}{}_{i,j}\right)$$

if the (n+1)-th layer is the output layer 313, wherein f' is the first derivative of the activation function, and $$t^{(n+1)}{}_j$$

is the comparison training value for the j-th node of the output layer 313.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 4:
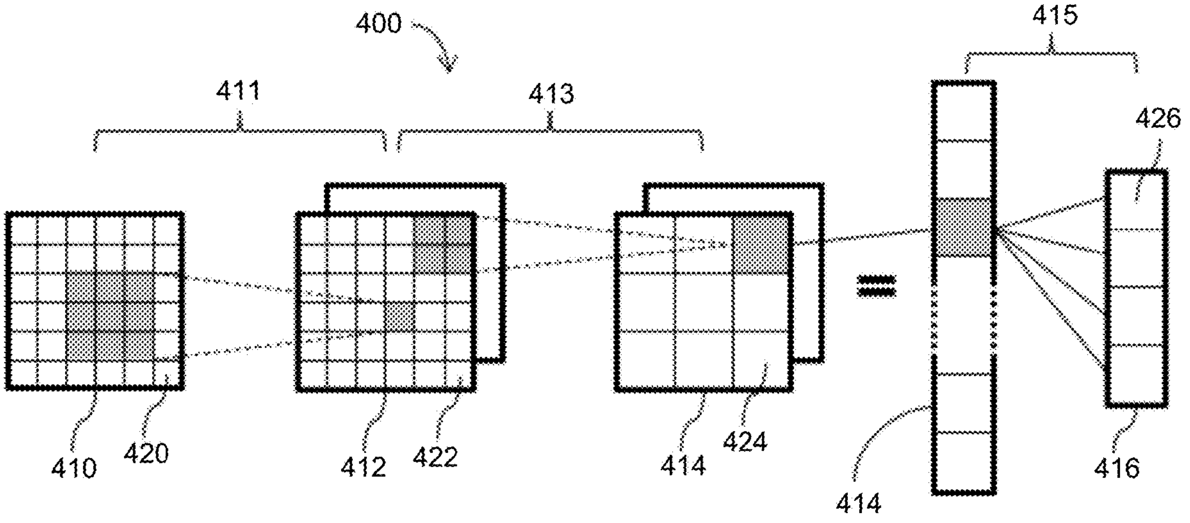
FIG. 4 shows a convolutional neural network that may be used to implement one or more embodiments.

FIG. 4 shows an embodiment of a convolutional neural network 400 that may be used to implement one or more machine learning models described herein. In the displayed embodiment, the convolutional neural network comprises

400 an input node layer 410, a convolutional layer 411, a pooling layer 413, a fully connected layer 414 and an output node layer 416, as well as hidden node layers 412, 414. Alternatively, the convolutional neural network 400 can comprise several convolutional layers 411, several pooling layers 413 and several fully connected layers 415, as well as other types of layers. The order of the layers can be chosen arbitrarily, usually fully connected layers 415 are used as the last layers before the output layer 416.

In particular, within a convolutional neural network 400 nodes 420, 422, 424 of a node layer 410, 412, 414 can be considered to be arranged as a d-dimensional matrix or as a d-dimensional image. In particular, in the two-dimensional case the value of the node 420, 422, 424 indexed with i and j in the n-th node layer 410, 412, 414 can be denoted as x(n) [i,j]. However, the arrangement of the nodes 420, 422, 424 of one node layer 410, 412, 414 does not have an effect on the calculations executed within the convolutional neural network 400 as such, since these are given solely by the structure and the weights of the edges.

A convolutional layer 411 is a connection layer between an anterior node layer 410 (with node values x(n−1)) and a posterior node layer 412 (with node values x(n)). In particular, a convolutional layer 411 is characterized by the structure and the weights of the incoming edges forming a convolution operation based on a certain number of kernels. In particular, the structure and the weights of the edges of the convolutional layer 411 are chosen such that the values x(n) of the nodes 422 of the posterior node layer 412 are calculated as a convolution x(n)=K*x(n−1) based on the values x(n−1) of the nodes 420 anterior node layer 410, where the convolution*is defined in the two-dimensional case as $$x_k^{(n)}[i,j]=(K*x^{(n-1)})[i,j]=\sum_{i'}\sum_{j'}K[i',j']\cdot x^{(n-1)}[i-i',j-j'].$$

Here the kernel K is a d-dimensional matrix (in this embodiment, a two-dimensional matrix), which is usually small compared to the number of nodes 420, 422 (e.g., a 3×3 matrix, or a 5×5 matrix). In particular, this implies that the weights of the edges in the convolution layer 411 are not independent, but chosen such that they produce said convolution equation. In particular, for a kernel being a 3×3 matrix, there are only 9 independent weights (each entry of the kernel matrix corresponding to one independent weight), irrespectively of the number of nodes 420, 422 in the anterior node layer 410 and the posterior node layer 412.

In general, convolutional neural networks 400 use node layers 410, 412, 414 with a plurality of channels, in particular, due to the use of a plurality of kernels in convolutional layers 411. In those cases, the node layers can be considered as (d+1)-dimensional matrices (the first dimension indexing the channels). The action of a convolutional layer 411 is then a two-dimensional example defined as $$x^{(n)_b}[i,j]=\sum_a K_{a,b}*x^{(n-1)_a}[i,j]=\sum_a\sum_{i'}\sum_{j'}K_{a,b}[i',j']\cdot x^{(n-1)_a}[i-i',j-j']$$

where $x^{(n-1)_a}$ corresponds to the a-th channel of the anterior node layer 410, $x^{(n)_b}$ corresponds to the b-th channel of the posterior node layer 412 and Kab corresponds to one of the kernels. If a convolutional layer 411 acts on an anterior node layer 410 with A channels and outputs a posterior node layer 412 with B channels, there are A·B independent d-dimensional kernels $K_{a,b}$.

In general, in convolutional neural networks 400 activation functions are used. In this embodiment re ReLU (acronym for "Rectified Linear Units") is used, with R (z)=max (0, z), so that the action of the convolutional layer 411 in the two-dimensional example is $$x^{(n)_b}[i,j]=R\left(\sum_a (K_{a,b}*x^{(n-1)_a})[i,j]\right)=R\left(\sum_a\sum_{i'}\sum_{j'}K_{a,b}[i',j']\cdot x^{(n-1)_a}[i-i',j-j']\right)$$

It is also possible to use other activation functions, e.g., ELU (acronym for "Exponential Linear Unit"), LeakyReLU, Sigmoid, Tanh or Softmax.

In the displayed embodiment, the input layer 410 comprises 36 nodes 420, arranged as a two-dimensional 6×6 matrix. The first hidden node layer 412 comprises 72 nodes 422, arranged as two two-dimensional 6×6 matrices, each of the two matrices being the result of a convolution of the values of the input layer with a 3×3 kernel within the convolutional layer 411. Equivalently, the nodes 422 of the first hidden node layer 412 can be interpreted as arranged as a three-dimensional 2×6×6 matrix, wherein the first dimension correspond to the channel dimension.

The advantage of using convolutional layers 411 is that spatially local correlation of the input data can exploited by enforcing a local connectivity pattern between nodes of adjacent layers, in particular by each node being connected to only a small region of the nodes of the preceding layer.

A pooling layer 413 is a connection layer between an anterior node layer 412 (with node values x(n−1)) and a posterior node layer 414 (with node values x(n)). In particular, a pooling layer 413 can be characterized by the structure and the weights of the edges and the activation function forming a pooling operation based on a non-linear pooling function *f*. For example, in the two-dimensional case the values x(n) of the nodes 424 of the posterior node layer 414 can be calculated based on the values x(n−1) of the nodes 422 of the anterior node layer 412 as $$x^{(n)_b}[i,j]=f\left(x^{(n-1)}[id_1,jd_2],\ldots,x^{(n-1)_b}[(i+1)d_1-1,(j+1)d_2-1]\right)$$

In other words, by using a pooling layer 413 the number of nodes 422, 424 can be reduced, by re-placing a number d1·d2 of neighboring nodes 422 in the anterior node layer 412 with a single node 422 in the posterior node layer 414 being calculated as a function of the values of said number of neighboring nodes. In particular, the pooling function *f* can be the max-function, the average or the L2-Norm. In particular, for a pooling layer 413 the weights of the incoming edges are fixed and are not modified by training.

The advantage of using a pooling layer 413 is that the number of nodes 422, 424 and the number of parameters is reduced. This leads to the amount of computation in the network being reduced and to a control of overfitting.

In the displayed embodiment, the pooling layer 413 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 400 are fully connected layers 415. A fully connected layer 415 is a connection layer between an anterior node layer 414 and a posterior node layer 416. A fully connected layer 413 can be characterized by the fact that a majority, in particular, all edges between nodes 414 of the anterior node layer 414 and the nodes 416 of the posterior node layer are present, and wherein the weight of each of these edges can be adjusted individually.

In this embodiment, the nodes 424 of the anterior node layer 414 of the fully connected layer 415 are displayed both as two-dimensional matrices, and additionally as non-related nodes (indicated as a line of nodes, wherein the number of nodes was reduced for a better presentability). This operation is also denoted as "flattening". In this embodiment, the number of nodes 426 in the posterior node layer 416 of the fully connected layer 415 smaller than the number of nodes 424 in the anterior node layer 414. Alternatively, the number of nodes 426 can be equal or larger.

Furthermore, in this embodiment the Softmax activation function is used within the fully connected layer 415. By applying the Softmax function, the sum the values of all nodes 426 of the output layer 416 is 1, and all values of all nodes 426 of the output layer 416 are real numbers between 0 and 1. In particular, if using the convolutional neural network 400 for categorizing input data, the values of the output layer 416 can be interpreted as the probability of the input data falling into one of the different categories.

In particular, convolutional neural networks 400 can be trained based on the backpropagation algorithm. For preventing overfitting, methods of regularization can be used, e.g., dropout of nodes 420, . . . , 424, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m−2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

Figure 5:
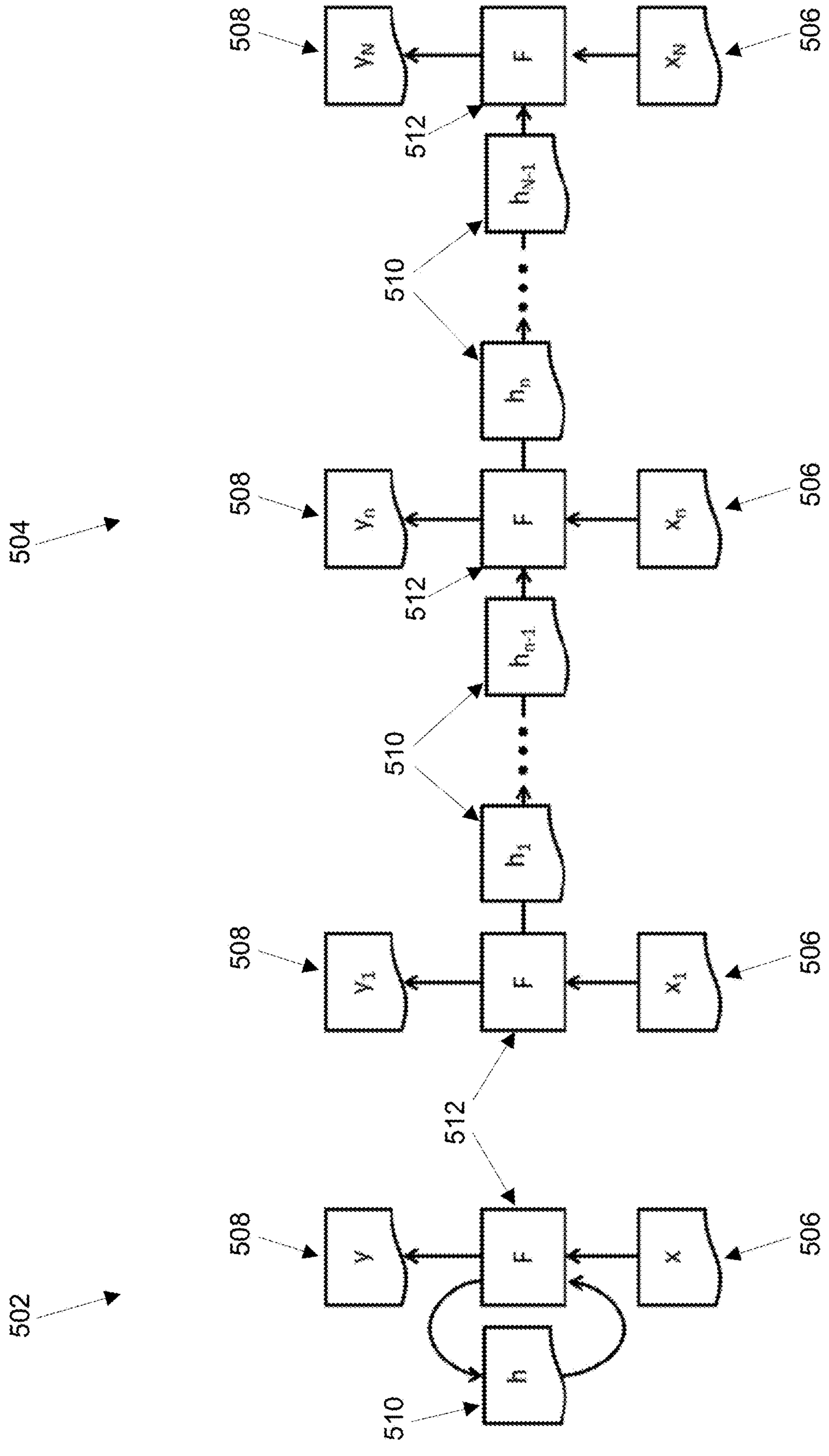
FIG. 5 shows a schematic structure of a recurrent machine learning model that may be used to implement one or more embodiments.

FIG. 5 shows the schematic structure of a recurrent machine learning model F, both in a recurrent representation 502 and in an unfolded representation 504, that may be used to implement one or more machine learning models described herein. The recurrent machine learning model takes as input several input datasets x, $X_1, \ldots, X_N$ 506 and creates a corresponding set of output datasets y, $y_1, \ldots, y_N$ 508. Furthermore, the output depends on a so-called hidden vector h, $h_1, \ldots, h_N$ 510, which implicitly comprises information about input datasets previously used as input for the recurrent machine learning model F 512. By using these hidden vectors h, $h_1, \ldots, h_N$ 510, a sequentiality of the input datasets can be leveraged.

In a single step of the processing, the recurrent machine learning model F 512 takes as input the hidden vector $h_{n-1}$ created within the previous step and an input dataset $X_n$. Within this step, the recurrent machine learning model F generates as output an updated hidden vector $h_N$ and an output dataset $y_n$. In other words, one step of processing calculates $(y_n, h_n)=F(X_n, h_{n-1})$, or by splitting the recurrent machine learning model F 512 into a part F(y) calculating the output data and F(h) calculating the hidden vector, one step of processing calculates $y_n=F^{(y)}(X_n, h_{n-1})$ and $h_n=F^{(h)}(x_n, h_{n-1})$. For the first processing step, $h_0$ can be chosen randomly or filled with all entries being zero. The parameters of the recurrent machine learning model F 512 that were trained based on training datasets before do not change between the different processing steps.

In particular, the output data and the hidden vector of a processing step depend on all the previous input datasets used in the previous steps. $y_n = F^{(v)}(X_n, F^{(h)}(X_{n-1}, h_{n-2}))$ and $h_n = F(h)(X_n, F(h)(X_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 2. Certain steps or functions of the methods and workflows described herein, including one or more of the steps or functions of FIG. 1 or 2, may be performed by a server or by another processor in a network-based cloud-computing system. Certain steps or functions of the methods and workflows described herein, including one or more of the steps of FIG. 1 or 2, may be performed by a client computer in a network-based cloud computing system. The steps or functions of the methods and workflows described herein, including one or more of the steps of FIG. 1 or 2, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 602 that may be used to implement systems, apparatuses, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 or 2 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1 or 2. Accordingly, by executing the computer program instructions, the processor 604 executes the method and workflow steps or functions of FIG. 1 or 2. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device.

It is also possible that the image acquisition device 614 and the computer 602 communicate wirelessly through a network. In a possible embodiment, the computer 602 can be located remotely with respect to the image acquisition device 614.

Any or all of the systems, apparatuses, and methods discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving one or more input medical images of a patient and text-based patient data of the patient; identifying one or more clinical tasks based on the text-based patient data using a language model; selecting one or more machine learning based models based on the one or more identified clinical tasks; performing one or more medical imaging analysis tasks based on the one or more input medical images using the one or more selected machine learning based models; generating a guided review of the one or more input medical images based on results of the one or more medical imaging analysis tasks; and outputting the guided review of the one or more input medical images.

Illustrative embodiment 2. The computer-implemented method of illustrative embodiment 1, wherein generating a guided review of the one or more input medical images based on results of the one or more medical imaging analysis tasks comprises: generating the guided review comprising a whole-image review of the one or more input medical images, a compartmental review depicting one or more anatomically cropped regions of the one or more input medical images, and a findings review depicting one or more pathologically cropped regions of the one or more input medical images.

Illustrative embodiment 3. The computer-implemented method of any one of illustrative embodiments 1-2, wherein outputting the guided review of the one or more input medical images comprises: presenting the guided review of the one or more input medical images to a user via a display device.

Illustrative embodiment 4. The computer-implemented method of any one of illustrative embodiments 1-3, wherein presenting the guided review of the one or more input medical images to a user via a display device comprises: depicting a cropped region depicting a first finding; receiving user input from the user confirming a decision on the first finding; and in response to receiving the user input, automatically depicting a cropped region depicting a second finding.

Illustrative embodiment 5. The computer-implemented method of any one of illustrative embodiments 1-4, wherein presenting the guided review of the one or more input medical images to a user via a display device comprises: presenting the guided review of the one or more input medical images according to parameters determined based on the one or more identified clinical tasks and outputs of the one or more selected machine learning based models.

Illustrative embodiment 6. The computer-implemented method of any one of illustrative embodiments 1-5, wherein the language model receives as input the text-based data and generates as output one or more vectors corresponding to the one or more or more clinical tasks.

Illustrative embodiment 7. The computer-implemented method any one of illustrative embodiments 1-6, wherein selecting one or more machine learning based models based on the one or more identified clinical tasks comprises: selecting the one or more machine learning based models from a database of pre-trained machine learning based models, the pre-trained machine learning based models comprising machine learning based models for performing different medical imaging analysis tasks and machine learning based models with different sensitivity.

Illustrative embodiment 8. The computer-implemented method of any one of illustrative embodiments 1-7, wherein the one or more input medical images comprise one or more PCCT (photon-counting computed tomography) images.

Illustrative embodiment 9. The computer-implemented method of any one of illustrative embodiments 1-8, wherein the language model is an LLM (large language model).

Illustrative embodiment 10. An apparatus comprising: means for receiving one or more input medical images of a patient and text-based patient data of the patient; means for identifying one or more clinical tasks based on the text-based patient data using a language model; means for selecting one or more machine learning based models based on the one or more identified clinical tasks; means for performing one or more medical imaging analysis tasks based on the one or more input medical images using the one or more selected machine learning based models; means for generating a guided review of the one or more input medical images based on results of the one or more medical imaging analysis tasks; and means for outputting the guided review of the one or more input medical images.

Illustrative embodiment 11. The apparatus of illustrative embodiment 10, wherein the means for generating a guided review of the one or more input medical images based on results of the one or more medical imaging analysis tasks comprises: means for generating the guided review comprising a whole-image review of the one or more input medical images, a compartmental review depicting one or more anatomically cropped regions of the one or more input medical images, and a findings review depicting one or more pathologically cropped regions of the one or more input medical images.

Illustrative embodiment 12. The apparatus of any one of illustrative embodiments 10-11, wherein the means for outputting the guided review of the one or more input medical images comprises: means for presenting the guided review of the one or more input medical images to a user via a display device.

Illustrative embodiment 13. The apparatus of any one of illustrative embodiments 10-12, wherein the means for presenting the guided review of the one or more input medical images to a user via a display device comprises: means for depicting a cropped region depicting a first finding; means for receiving user input from the user confirming a decision on the first finding; and means for automatically depicting a cropped region depicting a second finding in response to receiving the user input.

Illustrative embodiment 14. The apparatus of any one of illustrative embodiments 10-13, wherein the means for presenting the guided review of the one or more input medical images to a user via a display device comprises: means for presenting the guided review of the one or more input medical images according to parameters determined based on the one or more identified clinical tasks and outputs of the one or more selected machine learning based models.

Illustrative embodiment 15. A non-transitory computer-readable storage medium comprising instructions which, when executed by a computer, cause the computer to carry out operations comprising: receiving one or more input medical images of a patient and text-based patient data of the patient; identifying one or more clinical tasks based on the text-based patient data using a language model; selecting one or more machine learning based models based on the one or more identified clinical tasks; performing one or more medical imaging analysis tasks based on the one or more input medical images using the one or more selected machine learning based models; generating a guided review of the one or more input medical images based on results of the one or more medical imaging analysis tasks; and outputting the guided review of the one or more input medical images.

Illustrative embodiment 16. The non-transitory computer-readable storage medium of illustrative embodiment 15, wherein generating a guided review of the one or more input medical images based on results of the one or more medical imaging analysis tasks comprises: generating the guided review comprising a whole-image review of the one or more input medical images, a compartmental review depicting one or more anatomically cropped regions of the one or more input medical images, and a findings review depicting one or more pathologically cropped regions of the one or more input medical images.

Illustrative embodiment 17. The non-transitory computer-readable storage medium of any one of illustrative embodiments 15-16, wherein the language model receives as input the text-based data and generates as output one or more vectors corresponding to the one or more or more clinical tasks.

Illustrative embodiment 18. The non-transitory computer-readable storage medium of any one of illustrative embodiments 15-17, wherein selecting one or more machine learning based models based on the one or more identified clinical tasks comprises: selecting the one or more machine learning based models from a database of pre-trained machine learning based models, the pre-trained machine learning based models comprising machine learning based models for performing different medical imaging analysis tasks and machine learning based models with different sensitivity.

Illustrative embodiment 19. The non-transitory computer-readable storage medium of any one of illustrative embodiments 15-18, wherein the one or more input medical images comprise one or more PCCT (photon-counting computed tomography) images.

Illustrative embodiment 20. The non-transitory computer-readable storage medium of any one of illustrative embodiments 15-19, wherein the language model is an LLM (large language model).

The invention claimed is:

1. A computer-implemented method comprising:

receiving one or more input medical images of a patient and text-based patient data of the patient;

identifying one or more clinical tasks based on the text-based patient data using a language model;

selecting one or more machine learning based models based on the one or more identified clinical tasks;

performing one or more medical imaging analysis tasks based on the one or more input medical images using the one or more selected machine learning based models;

generating a guided review of the one or more input medical images, the guided review depicting one or more regions cropped from the one or more input medical images based on results of the one or more medical imaging analysis tasks; and presenting the guided review of the one or more input medical images to a user via a display device by:

depicting a cropped region of the one or more cropped regions depicting a first finding;

receiving user input from the user confirming a decision on the first finding; and in response to receiving the user input, automatically depicting a cropped region of the one or more cropped regions depicting a second finding.

2. The computer-implemented method of claim 1, wherein generating a guided review of the one or more input medical images comprises:

generating the guided review comprising a whole-image review of the one or more input medical images, a compartmental review depicting one or more anatomically cropped regions of the one or more input medical images, and a findings review depicting one or more pathologically cropped regions of the one or more input medical images.

3. The computer-implemented method of claim 1, wherein presenting the guided review of the one or more input medical images to a user via a display device comprises:

presenting the guided review of the one or more input medical images according to parameters determined based on the one or more identified clinical tasks and outputs of the one or more selected machine learning based models.

4. The computer-implemented method of claim 1, wherein the language model receives as input the text-based data and generates as output one or more vectors corresponding to the one or more or more clinical tasks.

5. The computer-implemented method of claim 1, wherein selecting one or more machine learning based models based on the one or more identified clinical tasks comprises:

selecting the one or more machine learning based models from a database of pre-trained machine learning based models, the pre-trained machine learning based models comprising machine learning based models for performing different medical imaging analysis tasks and machine learning based models with different sensitivity.

6. The computer-implemented method of claim 1, wherein the one or more input medical images comprise one or more PCCT (photon-counting computed tomography) images.

7. The computer-implemented method of claim 1, wherein the language model is an LLM (large language model).

8. An apparatus comprising:

means for receiving one or more input medical images of a patient and text-based patient data of the patient;

means for identifying one or more clinical tasks based on the text-based patient data using a language model;

means for selecting one or more machine learning based models based on the one or more identified clinical tasks;

means for performing one or more medical imaging analysis tasks based on the one or more input medical images using the one or more selected machine learning based models;

means for generating a guided review of the one or more input medical images, the guided review depicting one or more regions cropped from the one or more input medical images based on results of the one or more medical imaging analysis tasks; and means for presenting the guided review of the one or more input medical images to a user via a display device by:

means for depicting a cropped region of the one or more cropped regions depicting a first finding;

means for receiving user input from the user confirming a decision on the first finding; and means for automatically depicting a cropped region of the one or more cropped regions depicting a second finding in response to receiving the user input.

9. The apparatus of claim 8, wherein the means for generating a guided review of the one or more input medical images comprises:

means for generating the guided review comprising a whole-image review of the one or more input medical images, a compartmental review depicting one or more anatomically cropped regions of the one or more input medical images, and a findings review depicting one or more pathologically cropped regions of the one or more input medical images.

10. The apparatus of claim 8, wherein the means for presenting the guided review of the one or more input medical images to a user via a display device comprises:

means for presenting the guided review of the one or more input medical images according to parameters determined based on the one or more identified clinical tasks and outputs of the one or more selected machine learning based models.

11. A non-transitory computer-readable storage medium comprising instructions which, when executed by a computer, cause the computer to carry out operations comprising:

receiving one or more input medical images of a patient and text-based patient data of the patient;

identifying one or more clinical tasks based on the text-based patient data using a language model;

selecting one or more machine learning based models based on the one or more identified clinical tasks;

performing one or more medical imaging analysis tasks based on the one or more input medical images using the one or more selected machine learning based models;

generating a guided review of the one or more input medical images, the guided review depicting one or more regions cropped from the one or more input medical images based on results of the one or more medical imaging analysis tasks; and presenting the guided review of the one or more input medical images to a user via a display device by:

depicting a cropped region of the one or more cropped regions depicting a first finding;

receiving user input from the user confirming a decision on the first finding; and in response to receiving the user input, automatically depicting a cropped region of the one or more cropped regions depicting a second finding.

12. The non-transitory computer-readable storage medium of claim 11, wherein generating a guided review of the one or more input medical images comprises:

generating the guided review comprising a whole-image review of the one or more input medical images, a compartmental review depicting one or more anatomically cropped regions of the one or more input medical images, and a findings review depicting one or more pathologically cropped regions of the one or more input medical images.

13. The non-transitory computer-readable storage medium of claim 11, wherein the language model receives as input the text-based data and generates as output one or more vectors corresponding to the one or more or more clinical tasks.

14. The non-transitory computer-readable storage medium of claim 11, wherein selecting one or more machine learning based models based on the one or more identified clinical tasks comprises:

selecting the one or more machine learning based models from a database of pre-trained machine learning based models, the pre-trained machine learning based models comprising machine learning based models for performing different medical imaging analysis tasks and machine learning based models with different sensitivity.

15. The non-transitory computer-readable storage medium of claim 11, wherein the one or more input medical images comprise one or more PCCT (photon-counting computed tomography) images.

16. The non-transitory computer-readable storage medium of claim 11, wherein the language model is an LLM (large language model).

* * * * *